United States Patent
Aven et al.

(10) Patent No.: US 6,596,775 B2
(45) Date of Patent: Jul. 22, 2003

(54) ENHANCEMENT OF THE EFFICACY OF BENZOYLBENZENES

(75) Inventors: Michael Aven, Mainz (DE); Henry Van Tuyl Cotter, Trenton, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/939,740

(22) Filed: Aug. 28, 2001

(65) Prior Publication Data

US 2002/0028778 A1 Mar. 7, 2002

Related U.S. Application Data

(63) Continuation of application No. 09/484,288, filed on Jan. 18, 2000.
(60) Provisional application No. 60/117,920, filed on Jan. 29, 1999.

(51) Int. Cl.$^7$ ............................................. A01N 35/00
(52) U.S. Cl. ..................................................... 514/687
(58) Field of Search ......................................... 514/687

(56) References Cited

U.S. PATENT DOCUMENTS 6,127,570 A * 10/2000 Curtz et al.

FOREIGN PATENT DOCUMENTS

| EP | 899255 | * | 3/1999 |
| EP | 967196 | * | 12/1999 |
| EP | 1023834 | * | 8/2000 |
| WO | 0072677 | * | 12/2000 |
| WO | 0072678 | * | 12/2000 |
| WO | 0076317 | * | 12/2000 |

* cited by examiner

*Primary Examiner*—Paul J. Killos
(74) *Attorney, Agent, or Firm*—Keil & Weinkauf

(57) ABSTRACT

The invention relates to method for the enhancement of the activity and/or systemicity of fungicidal compositions containing at least one benzoylbenzene of formula I

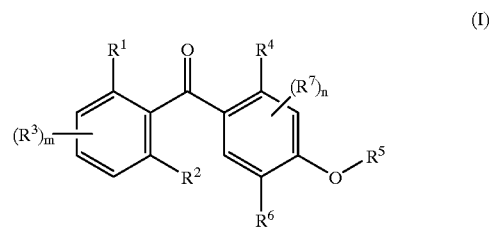

(I)

wherein
R$^1$ through R$^7$, m and n are as defined in claim 1,
with the aid of one or more adjuvants selected from the group consisting of
(a) alkylpolyglycosides, alkenyl succinic acid derivatives, dialkyl sulfosuccinates, polyvinylpyrrolidones, perfluoroalkyl acids derivatives, perfluoro(C$_{3-20}$)alkyl esters of carboxylic acids, and mixtures thereof;
(b) alkoxylated alcohols, amines or acids;
(c) water-immiscible polar aprotic solvents;
and to the use of such a composition as a fungicide.

24 Claims, No Drawings

ENHANCEMENT OF THE EFFICACY OF BENZOYLBENZENES

This application is a continuation of Ser. No. 09/484,288 filed Jan 18, 2000; which claims benefit to provisional application No. 60/117,920 filed Jan. 29, 1999.

BACKGROUND OF THE INVENTION

This invention concerns the enhancement of the efficacy of fungicidal benzoylbenzenes by addition of certain adjuvants, preparations through which this effect can be exploited as well as the combined use of these adjuvants and the fungicidal benzoylbenzenes in the control of phytopathogenic fungi and the plant diseases they cause.

As a rule inert ingredients must be used to bring crop protection agents, for example fungicidal compounds, into such a form that the user can apply them either as such or after dilution with water. The right choice of formulation type and of inert ingredients for that formulation type such as carriers for the formulation often determines to a significant extent whether the active ingredient can display its full efficacy on application.

The efficacy of the active components can often be improved by addition of other (active) ingredients. The observed efficacy of the combination of ingredients can sometimes be significantly higher than that would be expected from the amounts of the individual ingredients used (synergism).

The usual components of formulations such as carriers and inert ingredients (e.g. organic solvents, suspension agents, emulgators, wetting agents, solubilizing agents) which do not themselves possess pesticidal activity, however, do not usually lead to an unexpected increase in efficacy.

EP 0 727 141-A discloses fungicidal benzoylbenzenes compounds.

However, although these compounds are effective fungicides when applied to plants in conventional formulations it is desirable economically and environmentally to provide a means to lower the dose required for effective disease control.

SUMMARY OF THE INVENTION

The present invention relates to a method for the enhancement of the activity and/or systemicity of fungicidal compositions containing at least one benzoylbenzene of formula I

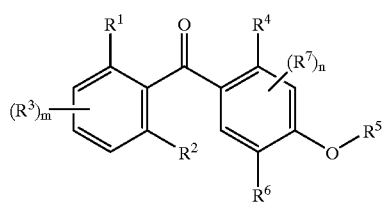

(I)

wherein $R^1$ represents a halogen atom, an optionally substituted alkyl, alkanoyloxy or alkoxy group; or a hydroxy group, $R^2$ represents a halogen atom, an optionally substituted alkyl group, $R^3$ represents a halogen atom or an optionally substituted alkyl group, m is 0 or an integer of 1 to 3;

$R^4$ independently represents a halogen atom, an optionally substituted alkyl or alkoxy group or a nitro group;

$R^5$ represents an optionally substituted alkyl group;

$R^6$ represents a halogen atom, a cyano, carboxy, hydroxy or nitro group or an optionally substituted alkyl, alkoxy, alkenyl, alkylthio, alkylsulphinyl, alkylsulphonyl or amino group;

$R^7$ represents a halogen atom or a nitro group, an optionally substituted alkyl, alkoxy, alkenyloxy, alkynyloxy, alkylthio, cycloalkyl, cycloalkyloxy, aryloxy group; and n is 0, 1 or 2;

characterized in that one or more adjuvants selected from the group consisting of (a) alkylpolyglycosides, alkenyl succinic acid derivatives, dialkyl sulfosuccinates, polyvinylpyrrolidones, perfluoroalkyl acids derivatives, perfluoro($C_{3-20}$)alkyl esters of carboxylic acids, and mixtures thereof;

(b) alkoxylated alcohols, amines or acids;

(c) water-immiscible polar aprotic solvents;

are added to the said composition.

Furthermore, the compositions used according to the present invention also expand the efficacy profile of the said benzoylbenzenes in so far as they can be successfully applied according to the present invention, with reduced application amounts, against fungal diseases for both curative and residual control.

Those and other objects and features of the invention will become more apparent from the detailed description set forth hereinbelow.

DETAILED DESCRIPTION OF THE PREFERRED EMBODIMENTS

It has now been found that, surprisingly, the effective amounts of fungicidal benzoylbenzenes of formula I which must be applied can be lowered considerably, with respect to the amounts usually required to achieve the same fungicidal effect, if these fungicidal compounds or their formulations are applied in combination with certain adjuvants selected from the group consisting of (a) alkylpolyglycosides, alkenyl succinic acid derivatives, dialkyl sulfosuccinates, polyvinylpyrrolidones, perfluoroalkyl acids derivatives, perfluoro($C_{3-20}$)alkyl esters of carboxylic acids, and mixtures thereof;

(b) alkoxylated alcohols, amines or acids; and (c) water-immiscible polar aprotic solvents.

The biological activity of the active ingredient of formula I can be increased by including any of these adjuvants in the spray dilution or directly in the formulation. An adjuvant is defined here as a substance which can increase the biological activity of an active ingredient but is not itself significantly biologically active.

The term 'fungicidal composition' as used herein includes both concentrated formulations and diluted mixtures (tank-mix).

Preferred compounds of formula I are the benzoylbenzenes of formula IA,

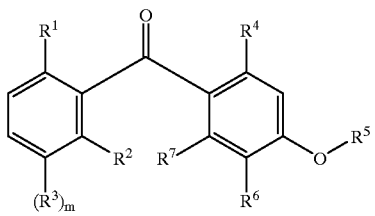

(IA)

wherein
- $R^1$ represents a chlorine atom, a methyl, trifluoromethyl, methoxy or a hydroxy group, most preferred a methoxy group;
- $R^2$ represents a chlorine atom or a methyl group;
- $R^3$ represents a bromo or chloro atom, a methyl, trifluoromethyl or nitro group;
- $R^4$ represents a methyl group;
- $R^5$ represents an alkyl group, preferably a $C_{1-4}$ alkyl group, in particular a methyl group;
- $R^6$ and $R^7$ each independently represent an alkoxy group which may be substituted by a phenyl, alkylphenyl or halophenyl group, preferably a $C_{1-6}$ alkoxy group, in a particular a methoxy, ethoxy, propyloxy or butyloxy group, or a benzyl group in which the phenyl ring may be substituted by one or more halogen atoms or one or more alkyl groups; and
- m is 0 or 1.

Most preferred are the following benzoylbenzenes:
6'-butoxy-2,6-dichloro-4',5'-dimethoxy-2'-methylbenzophenone (coded BB-1); 2,6-dichloro-4',5'-dimethoxy-6'-(2-fluorobenzyloxy)-2'-methylbenzophenone (coded BB-2); 6'-benzyloxy-4',5'-dimethoxy-2,6-dimethyl-2'-methylbenzophenone (coded BB-3); and [3-bromo-2',6-dimethyl-2,4',5',6'-tetramethoxybenzophenone] 5-bromo-2',6-dimethyl-2,4,5',6'-tetramethoxybenzophenone (coded BB-4), most preferred BB-4.

The fungicidal compositions of this invention can comprise other compounds having biological activity in addition to the benzoylbenzenes of formula I, e.g. compounds having similar or complementary fungicidal activity or compounds having plant growth regulating, herbicidal or insecticidal activity.

The other fungicidal compounds can be, for example, those which are capable of combating diseases of cereals (e.g. wheat) such as those caused by Blumeria (Erysiphe), Puccinia, Septoria, Gibberella, Botrytis and Helminthosporium spp., seed and soil borne diseases and downy and powdery mildews on vines and powdery mildew and scab on apples, Botrytis on numerous crops, leaf spot diseases on numerous crops, rice blast and rice sheath blight. These mixtures of fungicides can have a broader spectrum of activity than the compound of general formula I alone.

Examples of the other fungicidal compounds are AC 382042, alanycarb, aldimorph, ampropylfos, andoprim, anilazine, azaconazole, azafenidin, azoxystrobin, benalaxyl, benodanil, benomyl, benzamacril, bialaphos, biloxazol, binapacryl, biphenyl, bitertanol, blasticidin S, Bordeaux mixture, bromuconazole, bupirimate, butenachlor, buthiobate, captafol, captan, carbendazim, carboxin, carpropamid, carvone, chinomethionate, chlorbenzthiazon, chlorfenazol, chloroneb, chloropicrin, chlorothalonil, chlozolinate, clozylacon, copper-containing compounds such as copper oxychloride, and copper sulfate, cufraneb, cycloheximide, cymoxanil, cypofuram, cyproconazole, cyprodinil, cyprofuram, debacarb, dichlofluanid, dichlone, dichloran, dichlorophen, diclobutrazol, diclocymet, diclomezine, dicloran, diethofencarb, difenoconazole, difenzoquat, diflumetorim, dimefluazole, dimethirimol, dimethomorph, diniconazole, dinocap, diphenylamin, dipyrithione, ditalimfos, dithianon, dodemorph, dodine, drazoxolon, edifenphos, epoxiconazole, etaconazole, ethirimol, ethoxyquin, etridiazole, famoxadone, fenapanil, fenamidone, fenaminosulph, fenarimol, fenbuconazole, fenfuram, fenhexamid, fenitropan, fenpicionil, fenpropidin, fenpropimorph, fentin, fentin acetate, fentin hydroxide, ferbam, ferimzone, fluazinam, fludioxonil, flumetover, fluoromid, fluquinconazole, flurprimidol, flusilazole, flusulfamide, flutolanil, flutriafol, folpet, fosetyl-aluminium, fuberidazole, furalaxyl, furametpyr, furcarbonil, furconazole-cis, furmecyclox, guazatine, hexachlorobenzol, hexaconazole, hydroxyisoxazole, hymexazole, IKF-916, imazalil, imibenconazole, iminoctadine, iodocarb, ipconazole, iprobenfos, iprodione, iprovalicarb, isoprothiolane, isovaledione, kasugamycin, RH-7281, kitazin P, kresoxim-methyl, mancozeb, maneb, mefenoxam, meferimzone, mepanipyrim, mepronil, metalaxyl, metconazole, methasulfocarb, methfuroxam, metiram, metomeclam, metominostrobon, metsulfovax, MON 65500, myclobutanil, myclozolin, neoasozin, nickel dimethyidithiocarbamate, nitrothalisopropyl, nuarimol, ofurace, organo mercury compounds, oxadixyl, oxamocarb, oxasulfuron, oxycarboxin, paclobutrazol, pefurazoate, penconazole, pencycuron, phenazineoxide, phosdiphen, phthalide, pimaricin, piperalin, polyoxin D, polyram, probenazole, prochloraz, procymidone, propamocarb, propiconazole, propineb, prothiocarb, pyracarbolid, pyrazophos, pyrifenox, pyrimethanil, pyroquilon, pyroxyfur, quinconazole, quinomethionate, quinoxyfen, quintozene, rabenazole, spiroxamine, SSF-126, SSF-129, streptomycin, sulfur, tebuconazole, tecloftalame, tecnazene, tetcyclacis, tetraconazole, thiabendazole, thicyofen, thifluzamide, thiophanate-methyl, thiram, tioxymid, tolclofosmethyl, tolylfluanid, triadimefon, triadimenol, triazbutil, triazoxide, trichlamid, tricyclazole, tridemorph, trifloxystrobin, triflumizole, triforine, triticonazole, uniconazol, validamycin A, vapam, vinclozolin, XRD-563, zarilamid, zineb, ziram.

In addition, the compositions according to the invention may contain at least one compound of formula I and any of the following classes of biological control agents such as viruses, bacteria, nematodes, fungi, and other microorganism which are suitable to control insects, weeds or plant diseases or to induce host resistance in the plants. Examples of such biological control agents are: *Bacillus thuringiensis, Verticillium lecanii, Autographica califomica* NPV, *Beauvaria bassiana, Ampelomyces quisqualis, Bacilis subtilis, Pseudomonas cholororaphis, Pseudomonas fluorescens, Steptomyces griseoviridis* and *Trichoderma harzianum.*

Moreover, the co-formulations according to the invention may contain at least one compound of formula I and a chemical agent that induces the systemic acquired resistance in plants such as for example nicotinic acid or derivatives thereof, 2,2-dichloro-3,3-dimethylcyclopropylcarboxylic acid or BION.

The adjuvants (a) are preferably selected from the group consisting of alkylpolyglycosides, alkenyl succinic acid derivatives, dialkyl sulfosuccinates, perfluoro($C_{6-18}$) alkylphosphonic acids, perfluoro($C_{6-18}$) alkyl-phosphinic acids, perfluoro($C_{3-20}$)alkyl esters of carboxylic acids, and mixtures thereof.

Preferred alkylpolyglycosides (APG) are as a rule obtainable from a acid-catalyzed Fischer reaction of starch or glucose syrups with fatty alcohols, in particular $C_{8-18}$ alcohols. Most preferred are $C_{8-10}$ and $C_{12-14}$ alkylpolyglycosides having a degree of polymerization of 1.3 to 1.6., in particular 1.4 or 1.5. These APGs are commercially available for example under the tradenames Agrimul® and Glucopon®, which are APGs diluted with water, in particular Glucopon® 215CSUP or Glucopon® 600CSUP from Henkel KGaA or Atplus®430, Atplus®435, Atplus®450, Atplus®469, which are APGs diluted with hydrotrope agents, from Uniqema (formerly ICI Surfactants).

Preferred alkenyl succinic acid derivatives are compounds of formula

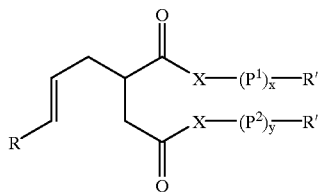

or salts thereof, in which

R represents a $C_{4-18}$ alkyl group, in particular a hexyl, heptyl or dodecyl group;

X represents O or $N(C_{1-6}$ alkyl)

$P^1$ and $P^2$ each represent a polymer back bone selected from the formulae (1) and (2):

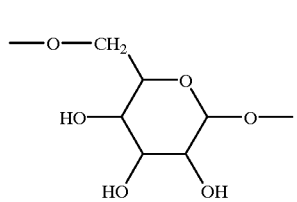

R' represents a hydrogen atom or an alkyl group, x represents 0 or an integer from 1 to 10, and y represents an integer from 1 to 10.

Preferred are alkenyl succinic acid diglucamides, alkenyl succinic acid alkoxylates and alkenyl succinic acid alkylpolyglykosides (WO 96/20203), in particular Atplus® ADG 1001 and Atplus® ADG 1201 obtainable from Uniqema.

Preferred polyvinylpyrrolidones (PVP) have an average molecular weight of more than 4000 g/mol, most preferred is a PVP having an average molecular weight of 8000 g/mol which is available as Agrimer® 15 from ISR Preferred dialkyl sulfosuccinates are sodium dialkyl sulfosuccinates as for example Aerosil® TO-100 from Cytec.

The adjuvant (b) includes pure alkoxylated alcohols, amines or acids, mixtures thereof as well as mixtures thereof with diluents and solid carriers, in particular clathrates thereof with urea.

The adjuvants (b), i.e. the alkoxylated alcohols, amines or acids are preferably based on alkoxy units having 2 carbon atoms, thus being a mixed ethoxylate, or 2 and 3 carbon atoms, thus being a mixed ethoxylate/propoxylate.

In a preferred alkoxylated alcohol, amine or acid, the alkoxylate chain may have at least 5 alkoxy moieties, suitably from 5 to 25 alkoxy moieties, preferably 5 to 20, in particular 5 to 15.

The alcohol moiety of the alcohol alkoxylates is as a rule derived from a $C_{9-18}$ aliphatic alcohol. Preferred alcohols are typically 50% by weight straight-chained and 50% by weight branched alcohols.

Particularly preferred are Neodol® (formerly Dobanol®) alcohol ethoxylates from Shell Chemical Co. Ltd. and Synperonic® alcohol alkoxylates from Uniqema (formerly ICI Surfactants), in particular Synperonic® 91-6.

Furthermore preferred alcohol alkoxylates are mono-branched alcohol ethoxylates such as Atplus® MBA 11-7 (branched $C_{11}$ alcohol ethoxylate with 7 ethoxy units) of Uniqema.

In case of solid formulations such as wettable powders (WP) or water-dispersible granules (WG), clathrates of alcohol ethoxylates with urea such as Atplus® S-620 of Uniqema are particularly preferred.

The aliphatic moieties of the amine alkoxylates may be straight-chained or branched. Preferably these compounds correspond to a oligomer of the following formula

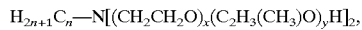

$$H_{2n+1}C_n-N[(CH_2CH_2O)_x(C_2H_3(CH_3)O)_yH]_2,$$

in which n is an integer from 9 to 20, in particular 12 to 18;

x is an integer from 2 to 15, in particular 3 to 10;

y is an integer from 0 to 12, in particular 0 to 10;

Of particular interest are those polyalkoxylated aliphatic amines, which are liquids at temperatures down to at least 20° C. having a viscosity of 100 to 1000 mPa.s at 25° C. The compounds which are commercially available under the trademark Armoblen® or Berol® (Akzo-Nobel), in particular Armoblen® 600 and Berol® 381 have been proven to be especially advantageous.

The aliphatic moieties of the acid may be straight-chained or branched. These adjuvants are as a rule obtainable by alkoxylation of fatty acids having 9–24, preferably 12–22 and in particular 14–20 C-atoms, with alkyleneoxide having 2–6, preferably 2–3 C-atoms. Preferably these compounds correspond to mixed random or block oligomers of the following formula

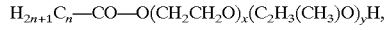

$$H_{2n+1}C_n-CO-O(CH_2CH_2O)_x(C_2H_3(CH_3)O)_yH,$$

in which r is 0 or 1, and the average of the indexes given is as follows:

n is an integer from 9 to 20, in particular 11 to 19;

x is an integer from 1 to 10, in particular 2 to 8; and y is an integer from 0 to 12, in particular 0 to 10.

The compounds which are commercially available as Henkel MeC12+6EO (Henkel KGaA) have been proven to be especially advantageous.

The adjuvants (c), i.e. the water-immiscible polar aprotic solvents are preferably $N-C_{2-16}$ alkyl-pyrrolidones, in particular $N-C_{6-14}$ alkyl-pyrrolidones, most preferred N-octyl- or N-dodecyl-pyrrolidone.

In a particularly preferred embodiment of the present invention two or more adjuvants selected from the groups (a), (b) and (c) are used to enhance the efficacy of the benzoylbenzenes of formula I. Most preferred one adjuvant (b), i.e. an alcohol or amine alkoxylate, in particular Synperonic® 91-6 or Atplus® MBA 11-7 and one adjuvant (c), i.e. a water-immiscible N-alkyl-pyrrolidone, in particular N-octyl-pyrrolidone or N-dodecyl-pyrrolidone are used to enhance the efficacy of the compounds of formula I.

The adjuvants which are usable according to the invention can be included in the formulation or also added in a suitable form with the preparation of the spray mix (tank mix). In this latter case, they are added preferably as a separate preparation in a mixture with a dispersing agent and, where desirable, with further adjuvants so as to ensure that a homogenous, stable spray mixture is formed.

Therefore, the invention relates to fungicidal formulations with at least one compound of formula I, adjuvants an/or carrier substances characterized by their containing, in addition to the conventional additives and carriers, one or more adjuvants, which have the capability of reducing the surface tension in the spray dilution to 40 mN/m or lower selected from the group:

(a) alkylpolyglycosides, alkenyl succinic acid derivatives, dialkyl sulfosuccinates, polyvinylpyrrolidones, perfluoroalkyl acids derivatives, perfluoro($C_{3-20}$)alkyl esters of carboxylic acids, and mixtures thereof;

(b) alkoxylated alcohols, amines or acids; and (c) water-immiscible polar aprotic solvents.

The fungicidal compounds can be applied as normal commercial formulations with which adjuvants according to the invention, and where desirable, additional additives such as antioxidants and emulgators, are mixed in.

The appropriate relative amounts of active ingredient of formula I and the adjuvant (a), (b) or (c) lie, in accordance with the invention, between 5:1 and 1:5000, preferably between 2:1 and 1:1000 and, in particular, between 1:1 and 1:500. Within certain limits, the fungicidal efficacy can be enhanced to a higher degree by the addition of larger amounts of the adjuvant (a), (b) or (c) as is shown in the experimental results described below.

In a preferred embodiment the adjuvant is added to the tank mix together with a the benzoylbenzene as formulation.

Therefore, the present invention relates also to a kit for the preparation of a spray mixture consisting of two separate containments:

(i) a containment which comprises at least one fungicide of formula I, conventional inert ingredients and carriers;

(ii) a containment which comprises at least one compound, which have the capability of reducing the surface tension in the spray dilution to 40 mN/m or lower selected from the group:

alkylpolyglycosides, alkenyl succinic acid derivatives, dialkyl sulfosuccinates, polyvinylpyrrolidones, perfluoroalkyl acids derivatives, perfluoro($C_{3-20}$)alkyl esters of carboxylic acids, and mixtures thereof;

alkoxylated alcohols, amines or acids; and water-immiscible polar aprotic co-solvents;

In a preferred embodiment the said kit will consist of two containers with dispensing means which allow the easy and correct addition of the active ingredient (i) and the adjuvant (ii) to the tank mix.

Recommended doses for various applications in the absence of an adjuvant are known for the fungicidal compounds of formula I. The efficacy thereof can be enhanced in accordance with the invention. Addition of the adjuvants suggested here can (depending on the active ingredient, the adjuvant and their respective amounts) reduce the amount of active ingredient per hectare required in these recommendations by half or more, whereby it becomes possible to control additional diseases at reasonable doses.

In a preferred embodiment the adjuvants (a), (b) or (c) in combination with the fungicide of formula I are applied at rates of 100 to 3000 mL/ha, preferably 200 to 2000 mL/ha, in particular 225 to 1400 mL/ha.

An important advantage is the rapid onset and the high persistency of activity on use of the new additives. This enlarges the period for application of the fungicide and makes its use more variable.

The fungicidal formulations according to the present invention can be used in combination with said additives prophylactically and curatively.

The adjuvants according to the invention, the compounds of formula I, and usual adjuvants and carriers can be processed to the preferably fluid or dispersible solid formulations known, for example, solutions, emulsions, WPs (wettable powders), WGs (water-dispersible granules), suspension concentrates, emulsion concentrates, low volume or ultra low volume preparations and granulates.

As well as fluid and/or solid carriers or solubilizing agents such as organic solvents like ketones, alcohols, fluid aliphatic, araliphatic or aromatic compounds, fine natural or synthetic silicates or carbonates, the preparations usually contain ionic and/or non-ionic surfactants which function as emulsifiers, dispersing agents or wetting agents. Antifoam, and antifreeze agents may be added. Suitable additives and carriers are described in the literature and well known to the persons skilled in the art.

A composition according to the invention preferably contains from 0.5% to 95% by weight (w/w) of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid.

The compositions may be manufactured into e.g. emulsifiable concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid additives. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. amyl alcohol, ethyleneglycol mono-and dimethyl ether, ketones such as cyclohexanone, strongly polar solvents such as N-methyl-2-pyrrolidone, N-cyclohexyl-2-pyrrolidone, or γ-butyrolactone, or epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are usually formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or non-ionic substances with good dispersing, emulsifying and wetting properties depending on the nature of the compound according to general formula I to be formulated. Surfactants may also mean mixtures of individual surfactants.

Preferred non-ionic surfactants are polyethyleneoxide-polypropyleneoxide block-copolymers of formula

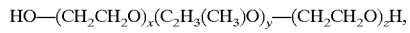

$HO-(CH_2CH_2O)_x(C_2H_3(CH_3)O)_y-(CH_2CH_2O)_zH$, in which
the sum of x and z is an integer from 1 to 80, in particular 2 to 75; and y is an integer from 10 to 70, in particular 20 to 60.

Most preferred are the Pluronic®-type block-copolymers, which are available from BASF AG, in particular Pluronic® PE 10500.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain, in addition to solid inert carrier, 3 to 10% w/w of dispersing and wetting agents and, where necessary, 0 to 10% w/w of stabilizer(s) and/or other additives such as antifoams. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of structure agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystallization or as antifreeze agents for water.

Aqueous solutions, dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are shown in the following formulations A to D:

| Formulation A: Suspension concentrate (100 g/L SC) | | |
|---|---|---|
| Component | Concentration [g/L] | Ingredient |
| active ingredient | 100.0 | Compound BB-4 |
| dispersant | 25.0 | Morwet ® D425[1] |
| dispersant | 5.0 | Pluronic ® PE 10500[2] |
| antifoam agent | 2.0 | Rhodorsil ® 426 R[3] |
| preservative | 1.5 | Proxel ® GXL[4] |
| structure agent | 3.0 | Rhodopol ® 23[3] |
| antifreeze agent | 30.0 | propylene glycol |
| water | to 1000 mL | |

[1] Witco Corporation, Houston Texas
[2] Tensid-Chemie, Köln/BASF AG, Ludwigshafen
[3] Rhodia, formerly Rhône-Poulenc GmbH, Frankfurt
[4] Zeneca GmbH, Frankfurt

| Formulation B: Suspension concentrate (200 g/L SC) | | |
|---|---|---|
| Component | Concentration [g/L] | Ingredient |
| active ingredient | 200.0 | BB-4 |
| dispersant | 25.0 | Morwet ® D425[1] |
| dispersant | 10.0 | Pluronic ® PE 10500[2] |
| antifoam agent | 2.0 | Rhodorsil ® 426 R[3] |
| preservative | 1.5 | Proxel ® GXL[4] |
| structure agent | 2.5 | Rhodopol ® 23[3] |
| antifreeze agent | 50.0 | propylene glycol |
| water | to 1000 mL | |

[1] Witco Corporation, Houston Texas
[2] Tensid-Chemie, Köln/BASF AG, Ludwigshafen
[3] Rhodia, formerly Rhône-Poulenc GmbH, Frankfurt
[4] Zeneca GmbH, Frankfurt The SC formulations A and B described above are mixed before application with water to give a spray mix with the desired concentration of active ingredient. An adjuvant selected from the groups (a), (b) and (c), in particular N-octylpyrrolidone, Synperonic® 91-6, Atplus® 469, Atplus® MBA 11-7 Atplus® ADG 1201, or Berol® 381, is added to the resulting tank mix.

| Formulation C: Emulsifiable concentrate (EC) | | |
|---|---|---|
| Component | Concentration [g/L] | Ingredient |
| active ingredient | 100.0 | BB-4 |
| dispersant | 30.0 | Sponto ® APF300[1] |
| dispersant | 1.5 | Sponto ® APF500[1] |
| solvent | to 1000 mL | Solventnaphtha |

[1] Witco Corporation, Houston Texas

The EC formulation described above is mixed before application with water to give a spray mix with the desired concentration of active ingredient. An adjuvant selected from the groups (a), (b) and (c), in particular N-octylpyrrolidone, Synperonic® 91-6, Atplus® 469, Atplus® MBA 11-7 Atplus® ADG 1201, or Berol® 381, is added to the resulting tank mix.

| Formulation D: Wettable Powder (200 g/kgL WP) | | |
|---|---|---|
| Component | Concentration [g/kg] | Ingredient |
| active ingredient | 200.0 | Compound BB-1 |
| dispersant | 30.0 | Tensiofix ® BCZ[5] |
| dispersant | 90.0 | Tensiofix ® LX-Spezial[5] |
| solid carrier | to 1000 g | China Clay GTY |

[5] Omnichem S.A., Belgium

The WP formulation described above is mixed before application with water to give a spray mix with the desired concentration of active ingredient. An adjuvant selected from the groups (a), (b) and (c), in particular Atplus® S-620, is added to the resulting tank mix.

It is also an object of the invention to suggest a method for the control of phytopathogenic fungi, characterized by the use of the compounds of formula I, in particular formula IA in combination with one or more compounds, which have the capability of reducing the surface tension in the spray dilution to 40 mN/m or lower selected from the group:

(a) alkylpolyglycosides, alkenyl succinic acid derivatives, dialkyl sulfosuccinates, polyvinylpyrrolidones, perfluoroalkyl acids derivatives, perfluoro($C_{3-20}$)alkyl esters of carboxylic acids, and mixtures thereof;

(b) alkoxylated alcohols, amines or acids;

(c) water-immiscible polar aprotic co-solvents.

A broad range of phytopathogenic fungi and plant diseases can be combated with the fungicidal mixtures according to the present invention. These include the classes Ascomycetes, Basidiomycetes, Oomycetes and Deuteromycetes. Therefore, they can be applied advantageously against a broad range of diseases in different crops. They may be applied as leaf, stem, root, fruit, into-water, seed dressing, nursery box or soil fungicides. The mixture according to the invention may be preferably applied for controlling phytopathogenic fungi of the genera:

Achlya, Alternaria, Balansia, Bipolaris, Blumeria, Botrytis, Cercospora, Cochliobolus, Curvularia, Cylindrocladium, Drechslera, Entyloma, Erysiphe, Fusarium, Gaeumannomyces, Gerlachia, Gibberella, Guignardia, Leptosphaeria, Magnaporthe, Microsphaera, Monilinia, Mucor, Mycosphaerella, Myrothecium, Nigrospora, Peronospora, Phaeosphaeria, Phoma, Phyllactinia, Phytophthora, Podosphaera, Pseudoperonospora, Pseudocercosporella, Puccinia, Pyrenophora, Pyricularia, Pythium, Rhizoctonia, Rhizopus, Rhynchosporium, Sarocladium, Sclerophthora, Sclerotium, Septoria, Sphaerotheca, Stagonospora, Tilletia, Uncinula, Ustilago, Ustilaginoidea, and Venturia, in particular the species *Blumeria graminis* f. sp. *tritici, Cercospora beticola, Septoria tritici, Erysiphe cichoracearum, Puccinia recondite, Pyrenophora teres* and *Uncinula necator*. The mixtures according to the invention are in particular applied for controlling the above phytopathogenic fungi on monocotylydoneous plants, such as barley and wheat, rice and turf grases or dicotylydoneous plants crops as pomefruits, stonefruits and vines as well as all kinds of vegetables and ornamentals.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

The test results described below demonstrate the enhancement in fungicidal efficacy and systemicity of the compounds of formula I by addition of the adjuvants (a), (b) or (c).

EXAMPLES

| Identity of Adjuvants used in Examples | | |
|---|---|---|
| Name | Abbreviation | Identity |
| Aerosil OT-100 (Cytec) | OT-100 | Sodium sulfosuccinate |
| Agsol ® EX 8 (ISP) | NOP | N-octylpyrrolidone |
| Armoblen ® 600 (Akzo-Nobel) | Ar 600 | Amine alkoxylate |
| Atplus ADG 1201 (Uniqema) | ADG 1201 | 50% $C_{12}$ alkenyl succinic anhydride diglucamide in propylene glycol |
| Atplus ® 469 (Uniqema) | 469 | Alkylpolysaccheride blend |
| Atplus ® MBA 11-7 (Uniqema) | MBA 11-7 | Branched alcohol ethoxylate |
| Berol ® 381 (Akzo-Nobel) | B 381 | Amine ethoxylate |
| Henkel MeC12 6EO | He 12-6 | Acid ethoxylate |
| Synperonic 91-6 (Uniqema) | S 91-6 | alcohol ethoxylate |

Greenhouse Evaluations for Fungicidal Efficacy

Disease: Wheat powdery mildew (WPM). Pathogen: *Blumeria graminis* f.sp. *tritici*

Test Procedure:

1. Wheat seed is planted in plastic pots and maintained in the greenhouse.

2. When the primary leaf (wheat) is fully expanded, formulated test compounds and adjuvants are sprayed with a single nozzle overhead track sprayer at a rate of 200 I/ha. Plants are then allowed to air-dry.

3. Inoculation precedes treatment by 2 days in the case of curative evaluations and follows treatment by 34 days in case of residual evaluations. For inoculation, plants are set up on greenhouse benches with bottom watering mats and inoculated by dusting them with conidia from powdery mildew infected plants (stock cultures at an age of 10–14 days). Between inoculation and treatment for curative evaluations and between treatment and inoculation for residual evaluations, plants are maintained in the greenhouse with bottom watering.

4. Disease on the primary leaf (wheat) as percent leaf area with disease symptoms/signs is evaluated about 7 days after inoculation. In the case of wheat, the tips and bases of the leaves are excluded from the evaluation.

Percent disease control is then calculated by the following formula:

$$\% \text{ disease control} = 100 - \frac{\% \text{ infection in treated plants}}{\% \text{ infection in untreated plants}} \times 100$$

Formulation, Reference Compounds and Controls

1. Formulated compounds are diluted using deionized water.

2. Two kinds of controls are included:

Plants treated with the solvent/surfactant solution and inoculated (Solvent Blank).

Untreated plants which are inoculated (Inoculated Control).

In antisporulation tests, inoculation preceeds compound application by three days.

Scale for Anti-Sporulation Effect:
+++=complete (no spore release);
++=strong;
+=moderate;
O=none.

Example 1

1000 ppm (1 ppm =1 mg/L) of Agsol® EX 8 (NOP) were added to a tank mix obtained from formulation C containing 100 g/L of BB-4. The observed efficacies with different rates are given in Table I:

TABLE I

| Compound: BB-4 | | WPM 2 day Curative Disease Control (%) | | WPM 4 day Residual Disease Control (%) | |
| --- | --- | --- | --- | --- | --- |
| Formulation | Rate (ppm) | No adjuvant | NOP (1000 ppm) | No adjuvant | NOP (1000 ppm) |
| EC 100 g/L | 25 | 89 | 96 | 99 | 100 |
| Formulation C | 5 | 73 | 94 | 58 | 99 |
|  | 1 | 42 | 80 | 27 | 90 |
|  | 0.2 | 22 | 57 | 9 | 55 |
| Adjuvant alone | 0 | — | 14 | — | 9 |

Example 2

1000 ppm of Synperonic 91-6 (S 91-6) were added to a tank mix obtained from formulation C containing 100 g/L of BB-4. The observed efficacies with different rates are given in Table II:

TABLE II

| Comp

TABLE X

| | | WPM Antisporulation Effect | | WPM 4 day Residual Disease Control (%) | |
|---|---|---|---|---|---|
| Compound: BB-4 | | | B 381 | | B 381 |
| Formulation | Rate (ppm) | No adjuvant | (1000 ppm) | No adjuvant | (1000 ppm) |
| EC 100 g/L | 25 | +++ | +++ | 99 | 100 |
| Formulation C | 5 | +++ | +++ | 99 | 100 |
| | 1 | ○ | ++ | 85 | 91 |
| | 0.2 | ○ | ○ | 35 | 40 |
| SC 200 g/L | 25 | +++ | +++ | 100 | 100 |
| Formulation B | 5 | + | +++ | 99 | 100 |
| | 1 | ○ | ++ | 81 | 96 |
| | 0.2 | ○ | + | 63 | 89 |
| Adjuvant alone | 0 | — | ○ | — | 9 |

Example 11

2000 ppm of Henkel MeC12+6EO (He 12-6) were added to a tank mix obtained from a formulation containing 100 g/L of BB-4. The observed efficacies with different rates are given in Table XI:

TABLE XI

| | | WPM 2 day Curative Disease Control (%) | | WPM 4 day Residual Disease Control (%) | |
|---|---|---|---|---|---|
| Compound: BB-4 | | | He 12-6 | | He 12-6 |
| Formulation | Rate (ppm) | No adjuvant | (2000 ppm) | No adjuvant | (2000 ppm) |
| EC 100 g/L | 25 | 83 | 92 | 100 | 100 |
| Formulation C | 5 | 60 | 76 | 83 | 90 |
| | 1 | 31 | 41 | 45 | 62 |
| | 0.2 | Not tested | Not tested | 20 | 29 |
| Adjuvant alone | 0 | — | 9 | — | 1 |

TABLE XIII

| | | WPM 2 day Curative Disease Control (%) | | WPM 4 day Residual Disease Control (%) | |
|---|---|---|---|---|---|
| Compound: BB-1 | | | S-620 | | S-620 |
| Formulation | Rate (ppm) | No adjuvant | (2000 ppm) | No adjuvant | (2000 ppm) |
| WP 200 g/kg | 625 | 22 | 93 | Not tested | Not tested |
| Formulation D | 125 | 22 | 89 | 98 | 100 |
| | 25 | 26 | 59 | 88 | 99 |
| | 5 | Not tested | Not tested | 50 | 91 |
| Adjuvant alone | 0 | — | 26 | — | 1 |

The above results clearly demonstrate that the adjuvants made an unexpectedly big improvement in the performance of the active ingredient.

What is claimed is:

1. A method for the enhancement of the activity and/or systemicity of fungicidal compositions comprising at least one benzoylbenzene of formula I 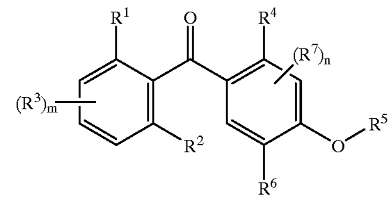 (I)

wherein $R^1$ represents a halogen atom, an optionally substituted alkyl, alkanoyloxy or alkoxy group; or a hydroxy group;

$R^2$ represents a halogen atom, an optionally substituted alkyl group;

$R^3$ represents a halogen atom;

m is 0 or an integer of 1 to 3;

$R^4$ independently represents a halogen atom, an optionally substituted alkyl or alkoxy group or a nitro group;

$R^5$ represents an optionally substituted alkyl group;

$R^6$ represents a halogen atom, a cyano, carboxy, hydroxy or nitro group or an optionally substituted alkyl, alkoxy, alkenyl, alkylthio, alkylsulphinyl, alkylsulphonyl or amino group;

$R^7$ represents a halogen atom or a nitro group, an optionally substituted alkyl, alkoxy, alkenyloxy, alkynyloxy, alkylthio, cycloalkyl, cycloalkyloxy, aryloxy group; and n is 0, 1, or 2;

and one or more adjuvants selected from the group consisting of (a) alkylpolyglycosides, alkenyl succinic acid derivatives, dialkyl sulfosuccinates, polyvinylpyrrolidones, perfluoroalkyl acids derivatives, perfluoro($C_3$–$C_{20}$)alkyl esters of carboxylic acids, and mixtures thereof;

(b) alkoxylated alcohols, amines or acids; and (c) water-immiscible polar aprotic solvents.

2. The method in accordance with claim 1, wherein the adjuvant (a) is selected from the group consisting of (i) alkylpolyglycosides which are obtainable from an acid-catalyzed Fischer reaction of starch or glucose syrups with fatty alcohols;

(ii) alkenyl succinic derivatives are compounds of formula 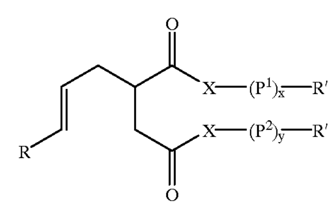 or salts thereof, in which R represents a $C_{4-18}$ alkyl group, in particular a hexyl, heptyl or dodecyl group;

X represents O or N($C_{1-6}$ alkyl);

$P^1$ and $P^2$ each represent a polymer back bone selected from the formulae (1) and (2):

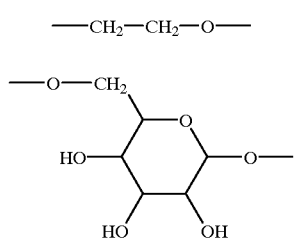

$R^1$ represents a hydrogen atom or an alkyl group;
x represents 0 or an integer from 1 to 10; and
y represents an integer from 1 to 10; and (iii) sodium dialkyl sulfosuccinates.

3. The method in accordance with claim 1, wherein the adjuvant (b) is selected from the group consisting of ethoxylated $C_{6-16}$ alcohols, $C_{3-14}$ alcohols being alkoxylated with ethyleneoxide and propyleneoxide units and $C_{10-20}$ amines being alkoxylated with ethyleneoxide and/or propyleneoxide units.

4. The method in accordance with claim 1, wherein the adjuvant (c) is selected from the group consisting of N-octylpyrrolidone, N-dodecylpyrrolidone and N-cyclohexylpyrrolidone.

5. The method in accordance with claim 1, wherein the adjuvant (a) is selected from the group consisting of perfluoro($C_{6-18}$)alkylphosphonic acids, perfluoro($C_{6-18}$)alkyl-phosphinic acids, perfluoro($C_{3-20}$)alkyl esters of carboxylic acids and mixtures thereof.

6. The method in accordance with claim 1, wherein the ratio of the crop protection active compound of formula I to said adjuvant is between 2:1 to 1:1000, preferably between 1:1 and 1:500.

7. The method in accordance with claim 1, wherein the benzoylbenzene is a compound of formula IA

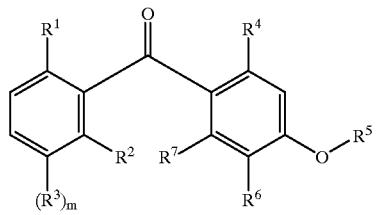

wherein
$R^1$ represents a halogen atom, a hydroxy, alkyl, alkanoyloxy or alkoxy group;
$R^2$ represents a halogen atom or an alkyl group;
$R^3$ represents a bromo or chloro atom;
$R^4$ independently represents an alkyl group;
$R^5$ represents an alkyl group;
$R^6$ represents an alkoxy group; and
$R^7$ represents an alkoxy group or benzyloxy group, in which the phenyl group is optionally substituted by one or more halogen atoms or one or more $C_{1-4}$ alkyl or $C_{1-4}$ alkoxy groups.

8. A fungicidal composition which comprises a carrier, one or more compounds of formula I,

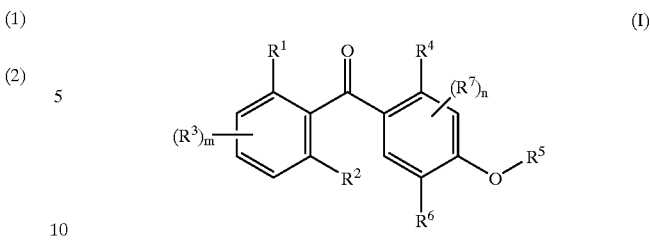

wherein $R^1$ through $R^7$, m and n are as defined in claim 1; and one or more adjuvants selected from the group consisting of (a) alkylpolyglycosides, alkenyl succinic acid derivatives, dialkyl sulfosuccinates, polyvinylpyrrolidones, perfluoroalkyl acids derivatives, perfluoro($C_3$–$C_{20}$)alkyl esters of carboxylic acids, and mixtures thereof;

(b) alkoxylated alcohols, amines or acids; and (c) water-immiscible polar aprotic solvents.

9. The fungicidal composition in accordance with claim 8, comprising (i) 50 to 400 parts of at least one compound of formula I;

(ii) 50 to 500 parts of at least one adjuvant selected from the groups (a), (b) and (c);

(iii) at least one surfactant selected from the groups (iii1) and (iii2);
(iii1) 5 to 75 parts of a non-ionic dispersant, and
(iii2) 10 to 100 parts of an anionic dispersant, (iv) up to 150 parts of one or more anti-freezing agents;

(v) up to 25 parts of a defoamer, and (vi) 200 to 800 parts of a carrier;

and optionally one or more additives selected from the groups (vii) to (ix):

(vii) 0.1 to 5.0 parts of at least one biocide;

(viii) 0.1 to 5.0 parts of at least one thickener; and (ix) 0.1 to 125.0 parts of at least one wetting agent.

10. A method for combating a phytopathogenic fungus at a locus which comprises treating said locus optionally upon dilution with water with a composition as claimed in claim 9.

11. A method according to claim 10, wherein said phytopathogenic fungus is the causative agent of powdery mildew disease.

12. The method of claim 1, wherein $R^3$ represents a bromo atom.

13. The composition of claim 8, wherein $R^3$ represents a bromo atom.

14. The method of claim 10, wherein $R^3$ represents a bromo atom.

15. The method in accordance with claim 7, wherein $R^3$ represents a bromo atom.

16. The method in accordance with claim 15, wherein the adjuvant (a) is selected from the group consisting of (i) alkylpolyglycosides which are obtainable from an acid-catalyzed Fischer reaction of starch or glucose syrups with fatty alcohols;

(ii) alkenyl succinic acid derivatives are compounds of formula

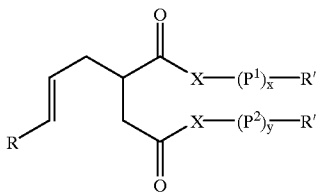

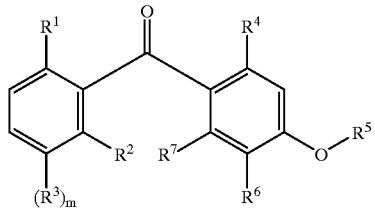

or salts thereof, in which
R represents a $C_{4-18}$ alkyl group, in particular a hexyl, heptyl or dodecyl group;
X represents O or $N(C_{1-6}$ alkyl);
$P^1$ and $P^2$ each represent a polymer back bone selected from the formulae (1) and (2):

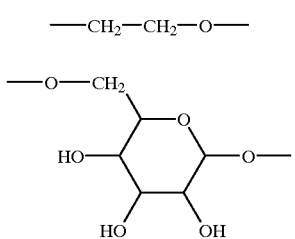

$R^1$ represents a hydrogen atom or an alkyl group;
x represents 0 or an integer from 1 to 10; and
y represents an integer from 1 to 10; and
(iii) sodium dialkyl sulfosuccinates.

17. The method in accordance with claim 15, wherein the adjuvant (b) is selected from the group consisting of ethoxylated $C_{6-16}$ alcohols, $C_{3-14}$ alcohols being alkoxylated with ethyleneoxide and propyleneoxide units and $C_{10-20}$ amines being alkoxylated with ethyleneoxide and/or propyleneoxide units.

18. The method in accordance with claim 15, wherein the adjuvant (c) is selected from the group consisting of N-octylpyrrolidone, N-dodecylpyrrolidone and N-cyclohexylpyrrolidone.

19. The method in accordance with claim 15, wherein the adjuvant (a) is selected from the group consisting of perfluoro($C_{6-18}$)alkylphosphonic acids, perfluoro($C_{6-18}$) alkylphosphonic acids, perfluoro($C_{3-20}$)alkyl esters of carboxylic acids and mixtures thereof.

20. The method in accordance with claim 15, wherein the ratio of the crop protection active compound of formula I to said adjuvant is between 2:1 to 1:1000, preferably between 1:1 to 1:500.

21. A fungicidal composition which comprises a carrier, one or more compounds of formula IA, wherein
$R^1$ represents a halogen atom, a hydroxy, alkyl, alkanoyloxy or alkoxy group;
$R^2$ represents a halogen atom or an alkyl group;
$R^3$ represents a bromo or chloro atom;
$R^4$ independently represents an alkyl group;
$R^5$ represents an alkyl group;
$R^6$ represents an alkoxy group; and
$R^7$ represents an alkoxy group or benzyloxy group, in which the phenyl group is optionally substituted by one or more halogen atoms or one or more $C_{1-4}$ alkyl or $C_{1-4}$ alkoxy groups; and
one or more adjuvants selected from the group consisting of
(a) alkylpolyglycosides, alkenyl succinic acid derivatives, dialkyl sulfosuccinates, polyvinylpyrrolidones, perfluoroalkyl acids derivatives, perfluoro($C_3$–$C_{20}$)alkyl esters of carboxylic acids, and mixtures thereof;
(b) alkoxylated alcohols, amines or acids; and
(c) water-immiscible polar aprotic solvents.

22. The fungicidal composition in accordance with claim 21, comprising
(i) 50 to 400 parts of at least one compound of formula IA;
(ii) 50 to 500 parts of at least one adjuvant selected from the groups (a), (b) and (c);
(iii) at least one surfactant selected from the groups (iii1) and (iii2);
(iii1) 5 to 75 parts of a non-ionic dispersant, and
(iii2) 10 to 100 parts of an anionic dispersant,
(iv) up to 150 parts of one or more anti-freezing agents;
(v) up to 25 parts of a defoamer, and
(vi) 200 to 800 parts of a carrier;
and optionally one or more additives selected from the groups (vii) to (ix):
(vii) 0.1 to 5.0 parts of at least one biocide;
(viii) 0.1 to 5.0 parts of at least one thickener; and
(ix) 0.1 to 125.0 parts of at least one wetting agent.

23. A method for combating a phytopathogenic fungus at a locus which comprises treating said locus optionally upon dilution with water with a composition as claimed in claim 22.

24. A method according to claim 23 wherein said phytopathogenic fungus is the causative agent of powdery mildew disease.

* * * * *